United States Patent
Monkowski et al.

(10) Patent No.: US 7,757,541 B1
(45) Date of Patent: Jul. 20, 2010

(54) TECHNIQUES FOR CALIBRATION OF GAS FLOWS

(75) Inventors: Joseph R. Monkowski, Danville, CA (US); Barton Lane, Pleasanton, CA (US)

(73) Assignee: Pivotal Systems Corporation, Pleasanton, CA (US)

( * ) Notice: Subject to any disclaimer, the term of this patent is extended or adjusted under 35 U.S.C. 154(b) by 235 days.

(21) Appl. No.: 11/855,052

(22) Filed: Sep. 13, 2007

Related U.S. Application Data

(60) Provisional application No. 60/844,495, filed on Sep. 13, 2006.

(51) Int. Cl.
*G01F 25/00* (2006.01)
(52) U.S. Cl. ...................................... 73/1.34
(58) Field of Classification Search ................. 73/1.34, 73/1.16, 861.04
See application file for complete search history.

(56) References Cited

U.S. PATENT DOCUMENTS

| | | | | | |
|---|---|---|---|---|---|
| 5,267,897 A | * | 12/1993 | Drees | ........................ | 454/225 |
| 5,744,695 A | * | 4/1998 | Forbes | ........................ | 73/1.35 |

* cited by examiner

*Primary Examiner*—Hezron Williams
*Assistant Examiner*—Tamiko D Bellamy
(74) *Attorney, Agent, or Firm*—Townsend and Townsend and Crew LLP

(57) ABSTRACT

An embodiment of a method in accordance with the present invention to determine the flow rate of a second gas relative to a first gas, comprises, setting a flow of a first gas to a known level, taking a first measurement of the first gas with a measurement technique sensitive to a concentration of the first gas, and establishing a flow of a second gas mixed with the first gas. A second measurement of the first gas is taken with a measurement technique that is sensitive to the concentration of the first gas, and the flow of the second gas is determined by a calculation involving a difference between the first measurement and the second measurement. In alternative embodiments, the first measurement may be taken of a flow of two or more gases combined, with the second measurement taken with one of the gases removed from the mixture. Certain embodiments of methods of the present invention may be employed in sequence in order to determine flow rates of more than two gases.

30 Claims, 5 Drawing Sheets

TECHNIQUES FOR CALIBRATION OF GAS FLOWS

CROSS-REFERENCE TO RELATED APPLICATION

The instant nonprovisional patent application claims priority to U.S. Provisional Patent Application No. 60/844,495, filed Sep. 13, 2006 and incorporated by reference herein for all purposes.

BACKGROUND OF THE INVENTION

Certain industrial processes depend on well controlled flows of gas. An example is in the field of semiconductor device manufacturing, which uses a wide variety of gases for processing silicon wafers into integrated circuits. Plasma etching is a particularly important semiconductor process that depends upon use of flows of a number of different gases. In plasma etching processes, various gases are introduced into a vacuum chamber and electrical power (typically in the form of radio frequency excitation) is used to ignite a plasma that creates reactive gas species. These reactive gas species etch patterns into the silicon wafer to define different components of the integrated circuit.

Because of the extremely small dimensions of the components of modern integrated circuits, effective manufacturing requires the use of gas flows exhibiting very stable and consistent characteristics, for example mass flow as measured in standard cubic centimeters per minute (sccm). Typically however, the electro-mechanical mass flow controllers used to control the flow of gases are prone to drift over time. The semiconductor industry is especially sensitive to these drifts since variations as small as a few percent can severely degrade the performance of the integrated circuit.

Accordingly, maintenance of stable gas flows requires frequent calibration of the mass flow controllers. Conventionally, calibration of the mass flow controllers is accomplished by introducing the gas into a vacuum chamber of a known volume while monitoring the pressure within that chamber. Based upon the known correlation between pressure, volume, and the mass of the gas introduced (which defines the number of molecules of the gas), the rise in pressure as the gas flows into the vacuum chamber can be monitored. This information regarding pressure change within the chamber can then be used to calibrate the mass flow controller.

One potential disadvantage of this conventional approach to calibrating gas flows is a loss in throughput. Specifically, the gas flow calibration procedure consumes highly valuable equipment time during which no productive processing can take place.

From the above, it is seen that improved gas flow calibration techniques are desired.

BRIEF SUMMARY OF THE INVENTION

An embodiment of a method in accordance with the present invention to determine the flow rate of a second gas relative to a first gas, comprises, setting a flow of a first gas to a known level, taking a first measurement of the first gas with a measurement technique sensitive to a concentration of the first gas, and establishing a flow of a second gas mixed with the first gas. A second measurement of the first gas is taken with a measurement technique that is sensitive to the concentration of the first gas, and the flow of the second gas is determined by a calculation involving a difference between the first measurement and the second measurement. In alternative embodiments, the first measurement may be taken of a flow of two or more gases combined, with the second measurement taken with one of the gases removed from the mixture. Certain embodiments of methods of the present invention may be employed in sequence in order to determine flow rates of more than two gases.

Various additional objects, features and advantages of the embodiments of the present invention can be more fully appreciated with reference to the detailed description and accompanying drawings that follow.

DETAILED DESCRIPTION OF THE INVENTION

Figure 1:
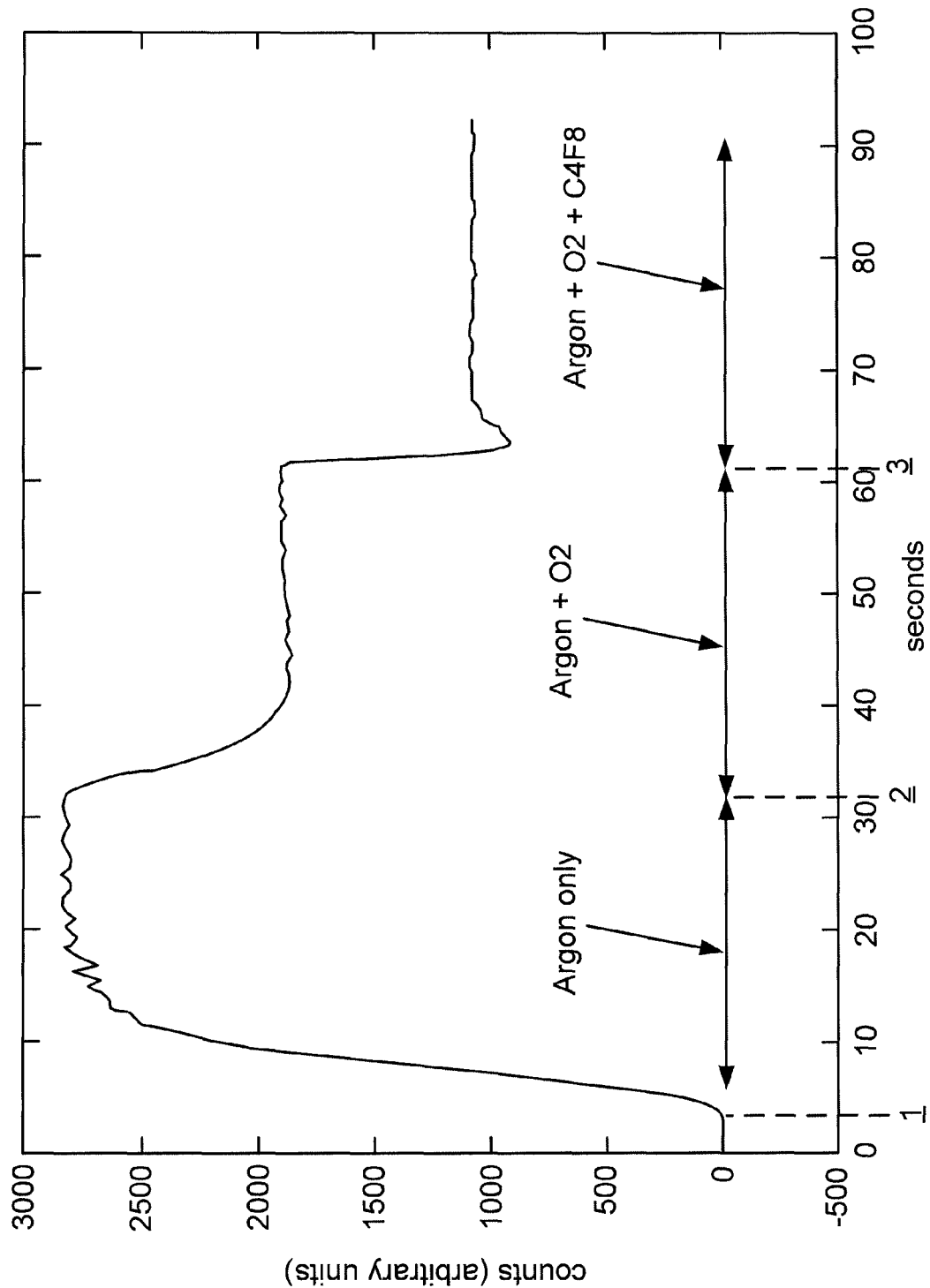
FIG. 1 plots optical emission spectroscopy (OES) readings versus time for an embodiment of a technique for calibrating gas flows in accordance with the present invention.

An embodiment of a method in accordance with the present invention to determine the flow rate of a second gas relative to a first gas, comprises, setting a flow of a first gas to a known level, taking a first measurement of the first gas with a measurement technique sensitive to a concentration of the first gas, and establishing a flow of a second gas mixed with the first gas. A second measurement of the first gas is taken with a measurement technique that is sensitive to the concentration of the first gas, and the flow of the second gas is determined by a calculation involving a difference between the first measurement and the second measurement. In alternative embodiments, the first measurement may be taken of a flow of two or more gases combined, with the second measurement taken with one of the gases removed from the mixture. Certain embodiments of methods of the present invention may be employed in sequence in order to determine flow rates of more than two gases.

If one measures a concentration of a pure gas, a certain reading will be obtained. If a second gas is introduced and mixed with the first gas at constant total pressure, the concentration of the first gas will decrease in proportion to the flow of the second gas. The amount of the decrease will depend on the relative flow of the second gas compared to the first. By measuring the concentration of the first gas by itself, and then measuring the concentration of this first gas after the introduction of the second gas, comparison of the first reading to the second reading would provide a measure of the relative concentration of the two gases. If the flow of the first gas is known with sufficient precision, the flow of the second gas can be calculated. If the flow of the first gas is not known with sufficient precision, the flow of the second gas relative to the first gas can be calculated.

A conventional approach to the calibration of gas flows is thus to mix the flows of two or more gases, and measure the relative concentrations of the various gases. Take, for example, the task of calibrating rates of flow of gases in a mixture of Ar, $O_2$, and $C_4F_8$ gases frequently employed in semiconductor plasma etching processes. It may be known with precision that a flow rate of argon (Ar) is 50 standard cubic centimeters per minute (sccm), and it is desired to establish flow rates of oxygen ($O_2$) and $C_4F_8$. Optical Emission Spectroscopy (OES) is a technique that is commonly employed to measure concentrations of gases in a plasma processing environment. A common conventional approach to establishing the $O_2$ and $C_4F_8$ flow rates would thus be to flow the Ar, $O_2$, and $C_4F_8$ gases together, and to measure the OES response of each of the gases in the mixture.

The gas flow calibration approach just described assumes either that the magnitude of at least one of the gas flows is known with precision, or that only the relative flow rates of the gases are needed to be determined. While one or more of these assumptions is frequently valid, in reality highly accurate measurements of gas concentrations can be difficult to achieve. While the gas concentrations need be measured with only relative, not absolute, accuracy, even this can pose a problem. Generally speaking, variation in concentration over time of different gases in a mixture will be similar. Thus if the OES reading for one gas in a mixture drifts upward, the same will likely happen for other gases in the mixture. However, this correlation is not always present, and even if the readings for both gases trend in the same direction, the amount of change can vary between the different gases. Thus in the specific example offered, the absolute OES readings of any one of the Ar, $O_2$, and $C_4F_8$ gases may vary over time. In addition, the OES readings of any one of the Ar, $O_2$, and $C_4F_8$ gases relative to one another may also vary over time. Accordingly, the accuracy of the gas flow calibration measurement may not be sufficiently high for certain applications.

Measurement of absolute concentration of a gas whether by OES or other techniques, especially when the gas is mixed with other gases, is difficult. In the case of OES, the brightness of a particular line will be influenced by details of the instrumental geometry and detector sensitivity. A first principles relation between the measured brightness and the concentration is usually impossible.

One solution to this problem is to look at the brightness of a line from a particular species when the concentration of the species is already known, and then to relate changes in brightness of this line to changes in concentration relative to the reference concentration. There are, however, long term drifts in the instrument response as well as possible short term changes due to inadvertent changes in the instrument geometry. These may introduce errors into such a measurement.

This problem is often addressed by comparing a line of interest to other lines, and then using these other lines to estimate the short- or long-term drifts. Such an approach, however, assumes that all lines drift together over time. This assumption is often not true.

Embodiments in accordance with the present invention adopt the approach of mixing gases and measuring concentrations. However, rather than taking concentration measurements on each of the relevant gases, the calibration of gas flows in accordance with embodiments of the present invention involves measurements made upon only one gas. In this manner, neither variation in sensitivity of the measuring instrument for a single gas over time, nor relative variation in sensitivity from one gas to another, will affect the measurement employed to calibrate the gas flows.

Figure 2:
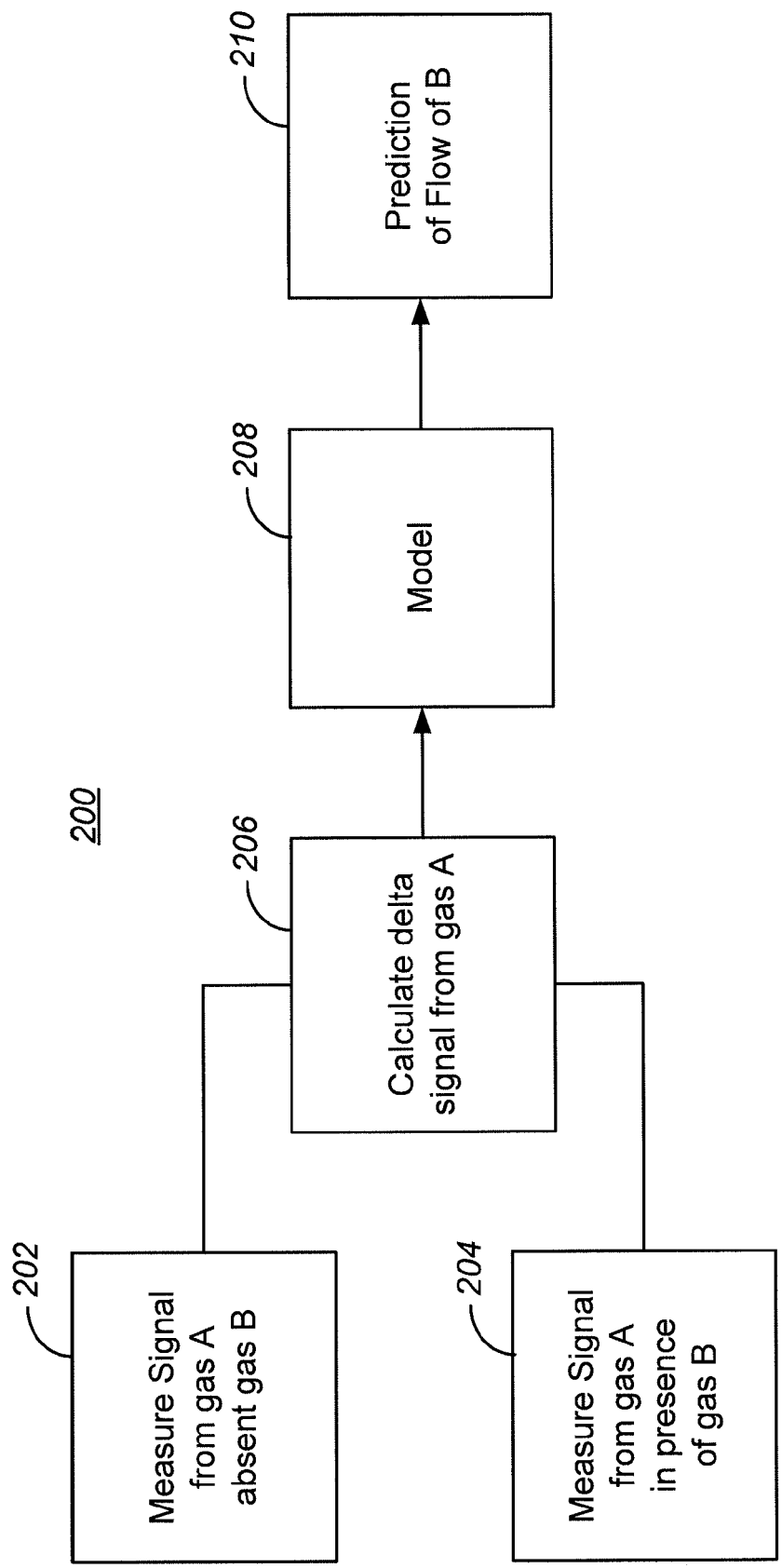
FIG. 2 is a simplified flow chart showing steps of a method in accordance with an embodiment of the present invention.

FIG. 2 is a simplified flow chart showing steps according to an embodiment of the present invention. In a first step 202 of flow 200, a signal indicating concentration of a first gas A, is measured in the absence of a condition, for example the absence of a flow of a second gas B. In a second step 204 of flow 200, the signal of the concentration of first gas A is again measured, but this time in the presence of the condition, for example a flow of a second gas B. In a third step 206, a difference (delta) between the signals taken in the first and second steps is calculated. In a fourth step 208, the delta calculated in the previous step is applied to a model. In accordance with one embodiment of the present invention, the model can comprise an empirical model, for example one or more calibration curves. In accordance with alternative embodiments of the present invention, the model can comprise a first principles model, as discussed in detail below. In a fifth step 210, application of the model results in a prediction of the magnitude of the second gas flow.

The approach of embodiments of the present invention can be understood in a series of examples, wherein a change in measured concentration of a gas being mixed with a second gas, is employed to deduce the flow of the second gas. In the simplest case, the first and second gases are two noble gases that are atomic and unreactive. In this case, the flow of the second gas causes a dilution of the first gas if the pressure is maintained at a constant level.

Specifically, it is possible to derive an expression for the flow of the second gas in terms of the change in measured concentration of the first gas, if the first and second gases are non-reactive. The equation for the time dependence of the total number of particles of the first and second gases are given in the Equations (1) and (2) respectively below:

$$\frac{dN_1}{dt} = F_1 - \frac{N_1}{V} A_p v_{p,1} \qquad (1, 2)$$
$$\frac{dN_2}{dt} = F_2 - \frac{N_2}{V} A_p v_{p,2} \quad \text{where:}$$

$N_1$=total number of particles of the first gas;

$F_1$=flow of the first gas;

V=volume of the reactor, $A_p$=effective area of the pump;

$v_{p,1}$=average velocity of particles of the first gas normal to the pump;

$N_2$=total number of particles of the second gas;

$F_2$=flow of the second gas;

$v_{p,2}$=average velocity of particles of the second gas normal to the pump;

Under steady state conditions, equations (1) and (2) can be solved for the concentration of the gases in terms of the flow rates and the pumping volumes and speeds, yielding Equations (3) and (4) respectively below:

$$\frac{N_1}{V} = \frac{F_1}{A_p v_{p,1}} \qquad (3, 4)$$
$$\frac{N_2}{V} = \frac{F_2}{A_p v_{p,2}}$$

If the pressure is sufficiently high that the mean free path of the gas particles is less than the characteristic dimensions of the pumping region geometry, or if the gas particles have comparable masses, the average normal velocity of particles of the first gas is substantially equal to the normal velocity of the second gas. In such a case (typical for gases employed in semiconductor processing), the pumping area and gas average normal velocity terms can be eliminated, yielding giving equation (5) for the concentration of the first gas in terms of the flows and the total concentration of the first and second gases.

$$\frac{N_1}{V} = \frac{F_1}{F_1 + F_2} \frac{N_1 + N_2}{V} \quad (5)$$

If the pressure is held constant, the total concentration of the first and second gases is equal to the total concentration of first gas when it was the only gas present ($N_1^0$), as shown in Equation (6) below:

$$\frac{N_1 + N_2}{V} = \frac{N_1^0}{V} \quad (6)$$

Substituting equation (5) into equation (6), the ratio of the concentration of the first gas when diluted with the second gas, to the concentration of the first gas when pure, can then be written as equation (7) below:

$$\frac{N_1/V}{N_1^0/V} = \frac{F_1}{F_1 + F_2} \quad (7)$$

According to Equation (7), the ratio of the concentration of the first gas diluted with the second gas to the first gas when pure, can be expressed as a function of the ratio of the flow rate of the first gas to the combined flow rates of the first and second gases. Thus the relative flow rate of the second gas relative to the first gas can be determined, once the ratio of the concentration of the first gas when diluted, to the concentration to the first gas when pure, is measured. In many potential applications, for example where multiple gases are being flowed in a fixed ratio to perform semiconductor processing, it is sufficient to be able to detect a change in the relative flow rates of the gases, rather than an absolute magnitude in the flow rate of any particular gas.

Alternatively, where an absolute magnitude of the flow rate of the first gas is known, Equation (7) can be re-written as equation (8) and solved for the flow rate of the second gas:

$$F_2 = F_1 \frac{N_1^0/V - N_1/V}{N_1/V} \quad (8)$$

Equation (8) may be useful where the flow rate of the first gas is known with certainty, for example where the first gas is a noble or unreactive gas whose mass flow controller is not subject to deposition or to corrosive etching, and hence whose flow can be relied upon as accurate.

In the situation described above, any method for measuring the concentration of the first gas can be employed. Specifically, a method in accordance with an embodiment of the present invention will yield accurate results so long as the measurement does not lead to a reaction of between the two gases, or to evolution of other species from the walls of the measurement chamber. The accuracy of the method is limited only by the accuracy of the flow of the first gas, and the accuracy of the method used to measure the concentration of the first gas.

One technique for measuring concentration according to embodiments of the present invention, may involve use of a diagnostic plasma in a secondary chamber that is in fluid communication with the primary chamber in which main processing occurs. Specifically, FIG. 5 shows a simplified cross-sectional view of an apparatus 600 for use in measuring gas flows in accordance with such an embodiment.

Apparatus 600 includes a processing chamber 601 having walls 602 enclosing a volume having a plasma 615 present therein. Chamber 601 includes a first inlet 608 for receiving gas from a gas supply 610 regulated through a mass flow controller MFC 609. Chamber 601 also includes a second inlet 603 for receiving a second gas from a second gas supply 611 regulated through a second mass flow controller MFC 613. Chamber 601 further includes an outlet 617 in connection with a vacuum pump 612.

Figure 5:
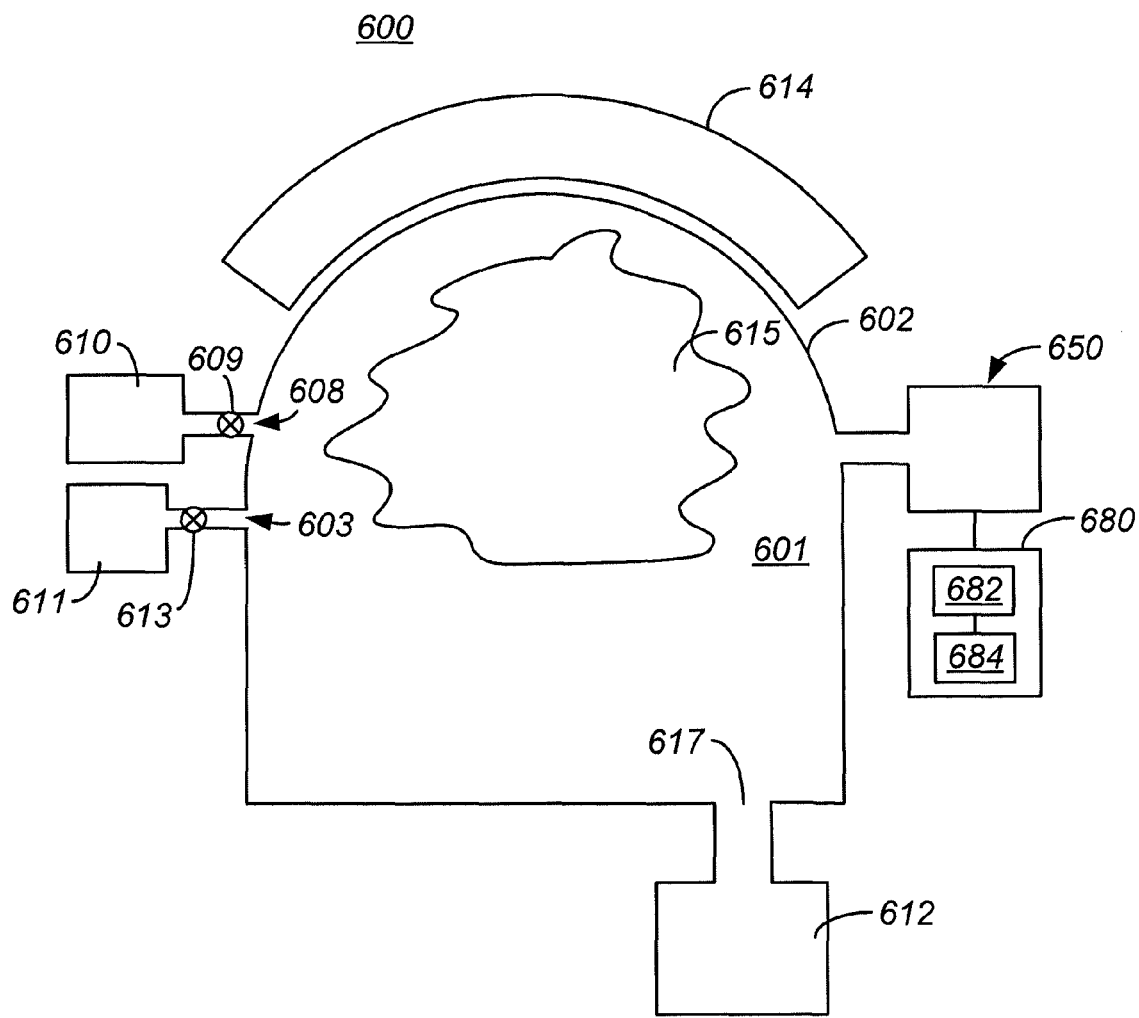
FIG. 5 is a simplified schematic diagram of an embodiment of an apparatus in accordance with the present invention for calibrating gas flows.

FIG. 5 also shows a gas concentration monitoring apparatus (sensor) 650 in accordance with an embodiment of the present invention, in fluid communication with chamber 601. Sensor 650 is also in electronic communication with host computer 680, which comprises processor 682 and computer readable storage medium 684. Computer readable storage medium 684 has code stored thereon configured to direct the processor to perform certain tasks, for example calculating the flow of a second gas from measurements of gases and gas mixtures present within the chamber in the manner described by embodiments of the present invention.

Figure 5A:
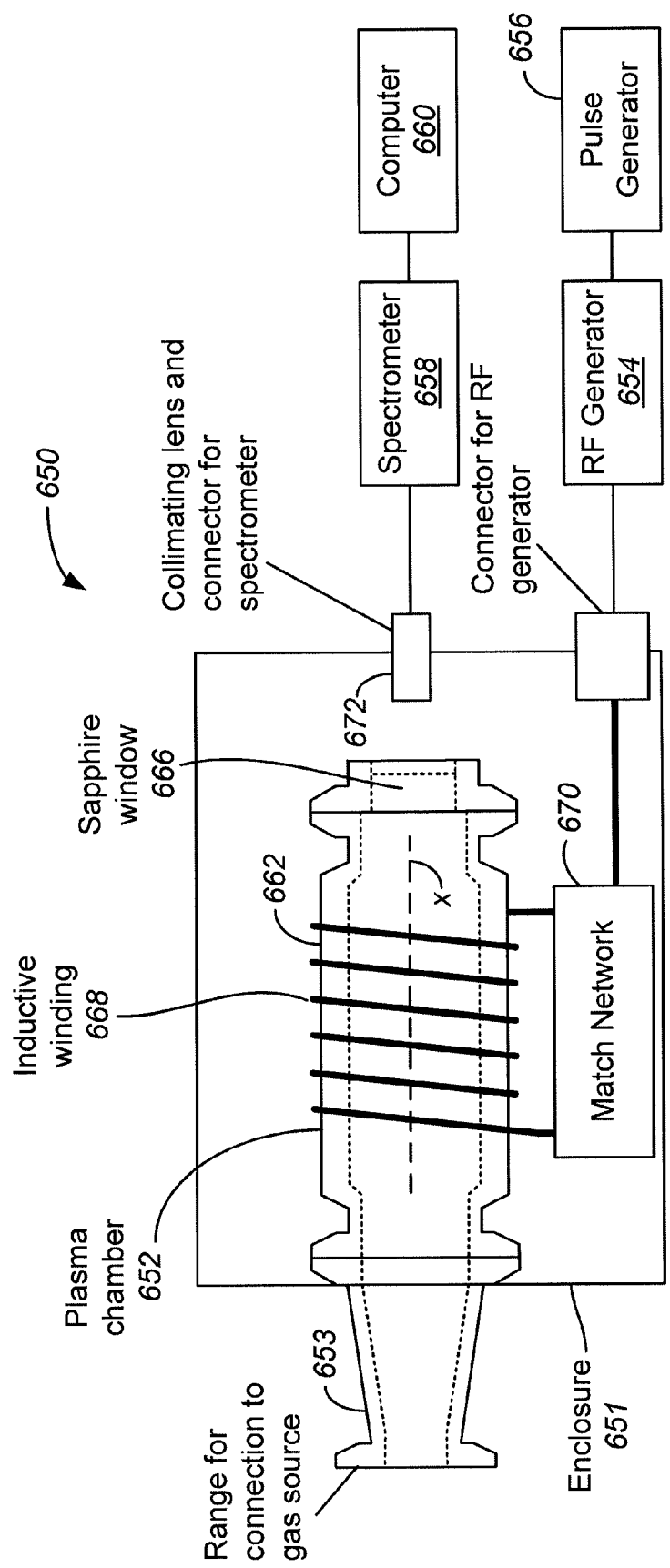
FIG. 5A is a simplified schematic diagram of an embodiment of a sensor for detecting gas concentration for use in accordance with embodiments of the present invention.

FIG. 5A shows an enlarged view of the sensing apparatus 650. Basic components of an embodiment of the apparatus of FIG. 5A in accordance with the present invention, include, an enclosure 651, plasma chamber 652 (where the molecules, molecular fragments, and atoms comprising the sampled gas are subjected to a plasma that dissociates enough of the multi-atom particles to create significant emission from individual atoms); a flange 653 connecting the chamber to a gas source, a RF (radio frequency) generator 654 that provides sufficient power into the plasma; and a spectrometer 658 that creates a spectrum from the plasma emission.

The apparatus of FIG. 5A also includes a computer or processor 660 to control the spectrometer. In particular, the computer or processor is configured to correlate intensity of emissions with relative concentrations of gases in the mixture. The computer/processor may also be configured to determine a stage of a process (such as endpoint) from the gas sample, based upon the relative concentrations of atoms in the gas or gas mixture.

Chamber 652 is comprised of materials that can reliably withstand a high density plasma comprising reactive elements such as fluorine and other halogens, metallic ions, and oxygen ions, while at the same time not contributing any harmful contamination to the process being monitored. In accordance with one embodiment, components exposed to the plasma include a tube 662, endpieces, and a window 666 in an endpiece through which the emission from the plasma can be detected by the spectrometer 658.

Although the plasma in the chamber can be generated with a number of different electrode configurations, one of the simplest and most effective is an inductive winding 668 around the $Al_2O_3$ tube 652. In such an embodiment, the wire comprising this winding should be of sufficient gauge to carry the large currents required for the high power plasmas. For example, in the specific embodiment of FIG. 5A, the winding is made from 12 American Wire Gauge (AWG) magnet wire.

During operation, the plasma is powered by a power source. Light emission from the plasma is passed through a spectrometer where the brightness of various spectral lines is determined. Atoms and molecules produce characteristic and unique spectra, and these can be used to measure the underlying concentration of species.

Absolute measurement of species concentration using such a technique is difficult. However, the brightness of lines is a function of the concentration of the species, and thus changes in brightness can be used to measure the change in the concentration of species.

Therefore, in the situation considered above involving the mixture of two noble gases, the change in the brightness of spectral lines originating from the first gas upon introduction of a second gas can be used to measure the flow rate of the second gas which is introduced. Because the measurements of a single gas are taken at points which are close together in time, the errors introduced by long term drifts are avoided.

Changes in brightness of spectral lines may occur not only from the change in the concentration of a species, but also from the change in parameters of the plasma such as the energy distribution of the electrons and the size of the plasma. Thus the function relating spectral brightness of a particular line to concentration relative to some reference concentration, may depart from a simple linear function.

The relation between spectral brightness and concentration can be derived from a model, for example a first principles model or an empirical model. In a first principles model, the energy distribution function of the plasma and the spatial size of the plasma could be determined through a solution to Boltzmann's equation for the electron energy distribution function and conservation equations for plasma species. This would yield a first principles prediction for the change in brightness of a particular spectral line of the first gas as a function of the concentration of the first and second gases. These concentrations would then be determined from the flows using the above equations. Together, this allows a first principles relation between the changes in brightness of a spectral line from the first gas. and the flows of the first and second gases.

Alternatively, the above equations, together with a calibrated MFC, could be used to empirically establish a relationship between the change in brightness of a spectral line of the first gas, and the change in concentration of the first gas and hence with the flows of the first and second gases. This relationship would be established by first determining the concentrations of the first gas as a function of the calibrated flows of the first and second gases. For example, knowing the total pressure and temperature of the gas and the flow rates, equation (5) can be used to determine the concentration of the first gas.

In the next step, the brightness of the spectral line emitted by the first gas would be measured for various flows of the second gas for a fixed flow of the first gas and compared to the brightness of the same spectral line for the pure first gas. These would form a table relating calibrated flows of the second gas for a fixed calibrated flow of the first gas, to concentrations of the first gas and brightness of a spectral line emitted by the first gas resulting from those calibrated flows In calibrating a new mass flow controller, a change in spectral brightness of the first gas could be measured and the empirical relationship inverted, to obtain the concentration of the first gas. From this concentration of the first gas, utilizing the above equations the flow of the second gas through the MFC being tested could be determined.

In applying the empirical model, the intermediate quantity of the concentration of the first gas is not needed. Accordingly, it is possible to create the simpler empirical relation between the flow rate of the second gas and the brightness of a particular spectral line emitted by the first gas, without computing the intermediary concentrations of the first or second gases.

In practice, a goal of embodiments according to the present invention is to measure the flow rates of reactive gases such as molecular oxygen and Freon, rather than relative flow rates of two noble gases. For example, consider the situation in which a carrier gas of Ar is mixed with a small flow of molecular oxygen. Spectral emission from a secondary diagnostic plasma is used. The plasma partly dissociates the molecular oxygen to atomic oxygen. Thus, rather than two species (Ar and $O_2$), three species (Ar+$O_2$+O) exist, and the concentration of Ar is reduced by the presence of both atomic and molecular oxygen.

In such a circumstance, it is still possible to employ a first principles model to determine the ratio of the flow of oxygen to argon. The equations developed for the mixture of the two noble gases can be modified by the addition of terms representing the loss of oxygen molecules to dissociation, and the gain of oxygen molecules by recombination of oxygen atoms. A new equation (9) for the change over time in the number of oxygen atoms (N3) is:

$$\frac{dN_3}{dt} = 2k_1 N_2 - k_2 N_3 \text{ where,} \tag{9}$$

$k_1$=dissociation rate of oxygen molecules $k_2$=recombination rate of atomic oxygen.

Equation (9) assumes that recombination occurs entirely on the reactor walls, and that the sites are fully occupied with oxygen atoms with the rate limiting step the reaction between a gas phase atom and an adsorbed oxygen atom. This equation also neglects the loss of atoms to the pump, since the wall area is typically larger than the pump effective area. These assumptions are not essential, but simplify the equations used in this illustration.

By algebraic manipulation of the combined equations (7) and (9) to yield equation (10) below:

$$F_2 = F_1 \frac{N_1^0/V - N_1/V}{N_1/V} \frac{1}{1 + 2k_1/k_2} \tag{10}$$

the flow of the second gas ($F_2$, here, oxygen) can be expressed in terms of the flows of the first gas ($F_1$, here, argon), the difference in concentration of the first gas, and a factor involving the ratio of the dissociation rate ($k_1$) to the recombination rate ($k_2$). Thus, measuring the change in the argon concentration between pure argon and argon diluted by a flow of molecular oxygen, allows determination of the input flow rate of the molecular oxygen using a first principles model, if the dissociation and recombination rates are known.

If the rates for dissociation and recombination are not known, it is still possible to employ the first principles model described above by making an additional measurement, in which the roles of argon and atomic oxygen as the first and second gases, are interchanged. In such a case, the concentration of the atomic oxygen is measured when no argon is present in the system. The atomic oxygen concentration is again measured when argon is introduced at a known flow rate.

The change in the concentration of atomic oxygen can be related to the flow rate of argon by equation (11):

$$\frac{N_3^0 - N_3}{N_3} = \frac{k_2}{2k_1} \frac{F_1}{F_2} \frac{1}{(1 + k_2/2k_1)} \quad (11)$$

Once the difference in atomic oxygen concentration between a pure oxygen case ($N_3^0/V$) and an oxygen mixed with argon case ($N_3/V$) can be determined through measurements, then equations (10) and (11) can be solved simultaneously to yield both the ratio $k_2/k_1$ and the ratio $F_1/F_2$.

As in the two noble gas example, the flow rate of the second gas is known as a function of the change in concentration of the first gas. In the case that the concentration is measured through spectroscopic means, either a model or a table can be used to relate the change in concentration of the first gas to the physically measurable change in brightness of a spectral line.

Embodiments in accordance with the present invention do not require performance of a second measurement in which the roles of argon and oxygen are reversed. Rather, changes in the brightness of a particular argon line can be tabulated as a function of the flow rate of oxygen using a calibrated MFC for a fixed flow rate of argon as determined by a calibrated MFC. Such a table can then be used to deduce the flow rate of the second gas (here, oxygen) through a test MFC, as a function of changes in brightness of the spectral lines of the first gas (here, argon). Such a table combines the relation between input flow rate of the second gas and the concentration of the first gas, and between the concentration of the first gas and changes in spectral brightness of the first gas, into a direct empirical relation between input flow rate of the second gas and changes in spectral brightness of the first gas. An example of such a TABLE is shown below:

TABLE

| Flow of Gas B (sccm) | Normalized Concentration of Gas A | Brightness of spectral line emitted by Gas A |
|---|---|---|
| 0 | 1 | 1000 |
| 10 | 0.9 | 850 |
| 20 | 0.8 | 700 |
| 30 | 0.7 | 550 |

In the above TABLE, the concentration of the gas A is shown for conceptual purposes only. In practice, the determination of the normalized concentration of gas A as a function of the flow of gas B is often difficult. However, this intermediate quantity is in fact unnecessary, as only a relation between the flow of gas B and the change in brightness of a spectral line emitted by gas A is needed to be determined. This relation can then be inverted to allow a determination of the flow of gas B once the spectral line brightness has been measured.

If an empirical model such as the table above is used to determine the flow rate of oxygen by measuring the change in brightness of an argon line when oxygen is mixed into an initially pure argon environment, performing a second measurement in which the roles of argon and oxygen are reversed can still be beneficial in reducing experimental error. Thus, a table would be created reflecting measurements using calibrated MFC's in which argon would be added to a pure oxygen environment. An oxygen line such as the 777 nm atomic oxygen line would be measured.

However, unlike the table above, if the MFC that was to be tested in the future was the MFC which metered oxygen, the change in the brightness of the 777 nm line would measured for several calibrated flow rates of oxygen into which would be diluted by one reference calibrated flow rate of argon. When testing an uncalibrated oxygen MFC, the measurement of the change in brightness of the 777 nm line would be performed for a particular setting on the oxygen MFC being tested with the reference setting for the diluting flow rate of argon used in constructing the table. The table would then be used to determine the flow rate of the calibrated oxygen MFC which produced this change in spectral brightness.

In the absence of experimental errors the two measurements, one with argon as the first gas and the other with oxygen as the first gas, would yield the same determination of the ratio of the flow rates of oxygen and argon. However given the inevitable presence of experimental errors the two independent determinations of the same physical quantity allow one to reduce these experimental errors either through simple averaging or through more sophisticated statistical means which exploited the historic empirically determined experimental errors associated with each of the two measurements.

The approach taken in accordance with embodiments of the present invention is illustrated in FIG. 1, which plots OES readings (brightness of an argon line) in an $Ar/O_2/C_4F_8$ mixture, over time. The "counts" shown on the y-axis of FIG. 1 are the readings taken for Ar gas only on an OES instrument. These counts are labeled as "arbitrary" because establishing an absolute value of concentration for any particular gas is extremely difficult, the relationship between counts and flow rate was not established for this particular example.

As shown in FIG. 1, starting at point 1 and for the first 30 seconds, only Ar is flowed. Starting at point 2 and during the next 30 seconds, the Ar flow is maintained, and the $O_2$ flow is maintained. Note that at point 2 the measured concentration of Ar drops from a steady state value of approximately 2800 counts, to a steady state value of approximately 1900 counts.

If the effect of introduction of the $O_2$ gas is merely to dilute the Ar, and the reading for the Ar is directly proportional to the concentration of the Ar, then the flow of $O_2$ may be calculated as shown in the equation (12) below:

1900(reading for Ar when $O_2$ is flowing)/2800(reading for Ar when no $O_2$ is flowing)=50 sccm(flow rate of Ar)/(50 sccm+$O_2$ flow) (12)

Solving this equation (12) for "$O_2$ flow" yields a result of 23.7 sccm.

In reality, the presence of $O_2$ will influence the Ar reading beyond just the dilutive effect. This is not a problem, however, since measurements of this effect can be made, and the calculations adjusted accordingly. Specifically, as discussed above the dissociation of molecular oxygen complicates the above calculation which is based purely on the dilution effect. Either a first principles model would need to be developed (such as the one illustrated above) involving a knowledge of the dissociation and recombination rates or a second measurement, or an empirical model in the form of a table of changes in spectral brightness versus oxygen flow rate would need to be constructed.

FIG. 1 shows that starting at point 3 and during the next 30 seconds, $C_4F_8$ is flowed with the Ar and $O_2$. Two options are available to determine a flow rate of $C_4F_8$ in the gas mixture. A first option is to measure the change in Ar reading relative to point 2 (between the second and third steps). Note that in this case, the $C_4F_8$ is introduced into a mixture of gases (Ar+$O_2$) rather than into a pure gas. This, however, does not present a problem as the OES measurement will still be performed on only a single gas (e.g., Ar) for both steps.

A second option for determining a flow rate of $C_4F_8$ in the gas mixture is to measure the change in $O_2$ reading (change in brightness of an oxygen line) relative to point 2 (between the second and third steps). Again, the important feature of both options is not the particular gas (Ar or $O_2$) whose concentration is being measured, but rather that the concentration of the same gas is being measured in each instance, separated by a short time interval where any drift will be negligible.

Relating the changes of either the brightness of the argon line or the brightness of the oxygen line upon addition of $C_4F_8$ to an argon/oxygen mixture, to the flow of $C_4F_8$, can be accomplished as described above through the use of series of measurements using calibrated MFCs. Such a table of changes in brightness of spectral lines of argon or oxygen as a function of $C_4F_8$ flow can then be used to deduce the $C_4F_8$ flow from the change in brightness for a test MFC.

The various steps described above can be performed in a different order. Thus in this example given, one could begin by flowing Ar and $O_2$, and then turn off the $O_2$, thus reversing the order of steps 1 and 2.

It is often desirable to construct a calibration curve for a test MFC, in which the true flow is plotted against the commanded flow for a number of flow settings. This can be done using the methods described above, by repeatedly determining the flow rates of a second gas for a series of commanded flows to the test MFC. In one example, a first gas would be flowed with increasing amounts of a second gas mixed in.

Alternatively, the brightness of a spectral line of the first gas can be measured as a function of an increasing series of flows of the second gas. The constant offset of this line of data points is subject to long term drifts and unintentional changes to the geometry of the sensor. However, calculating the slope of the brightness of the first gas versus second gas flow involves a sequence of calculations involving differences in brightness of the first gas. Such a method has two attractive features. First, this method addresses a common MFC problem dealing with the zero point. Second, this method utilizes several measurement points to determine the slope, thereby reducing some of the random noise in such measurements.

Figure 3:
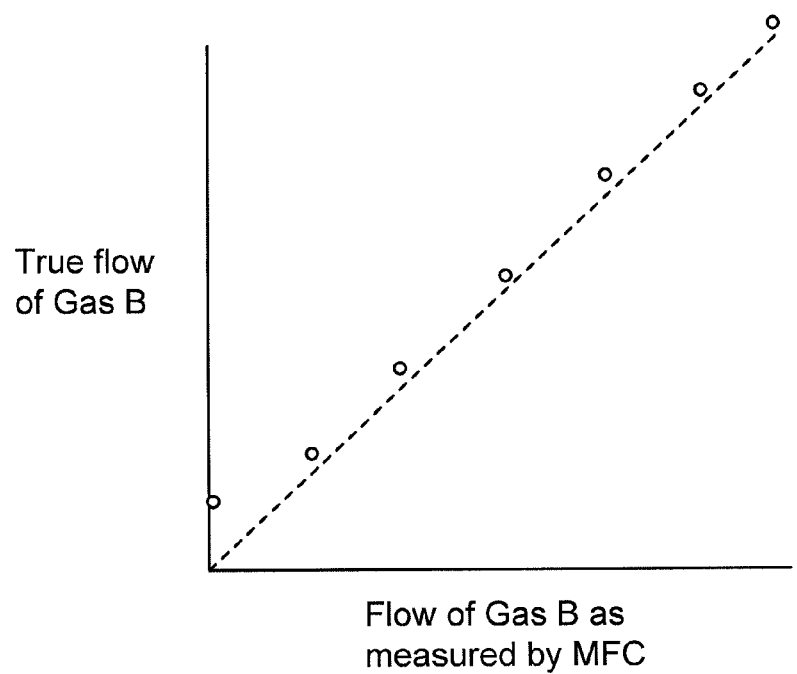
FIG. 3 plots the true flow of a gas through a mass flow controller versus the commanded flow of the gas, in a first hypothetical example.

FIG. 3 shows an example of the calibration curve for a hypothetical mass flow controller (MFC). Specifically, in FIG. 3 the flow commanded to the MFC is plotted on the horizontal axis, and the true flow as accurately measured is plotted on the vertical axis. The dotted line represents a line at 45 degrees. A perfectly operating MFC would yield the data points that all lay on this line.

For purposes of illustration, two possible deviations in MFC operation from the ideal state are considered. A first deviation is a constant offset of the data points from the ideal line. A second deviation occurs at very low flows where the curve is nonlinear.

Utilizing the instant method, both of these deviations from the test MFC can be determined. One example is to determine the deviations for an MFC through which $C_4F_8$ is flowing. Following the terminology of the previous examples, the first gas introduced into the chamber would be molecular oxygen, and the physical quantity measured would be the brightness of the 777 nm line of atomic oxygen.

The Freon gas $C_4F_8$ would be introduced in a succession of increasing flows, and the brightness of the 777 nm atomic oxygen line would be plotted versus the associated flow rate of the Freon gas. Since atomic oxygen reacts with the Freon gas to produce carbon monoxide (CO), it is expected that increasing the flow rate of Freon will deplete the atomic oxygen more rapidly than the simple dilution effect in the case of argon and oxygen. However, it is expected that the brightness of the atomic oxygen line will be linear with the flow of oxygen for Freon flow rates which are small in comparison to the oxygen flow rates.

Figure 4:
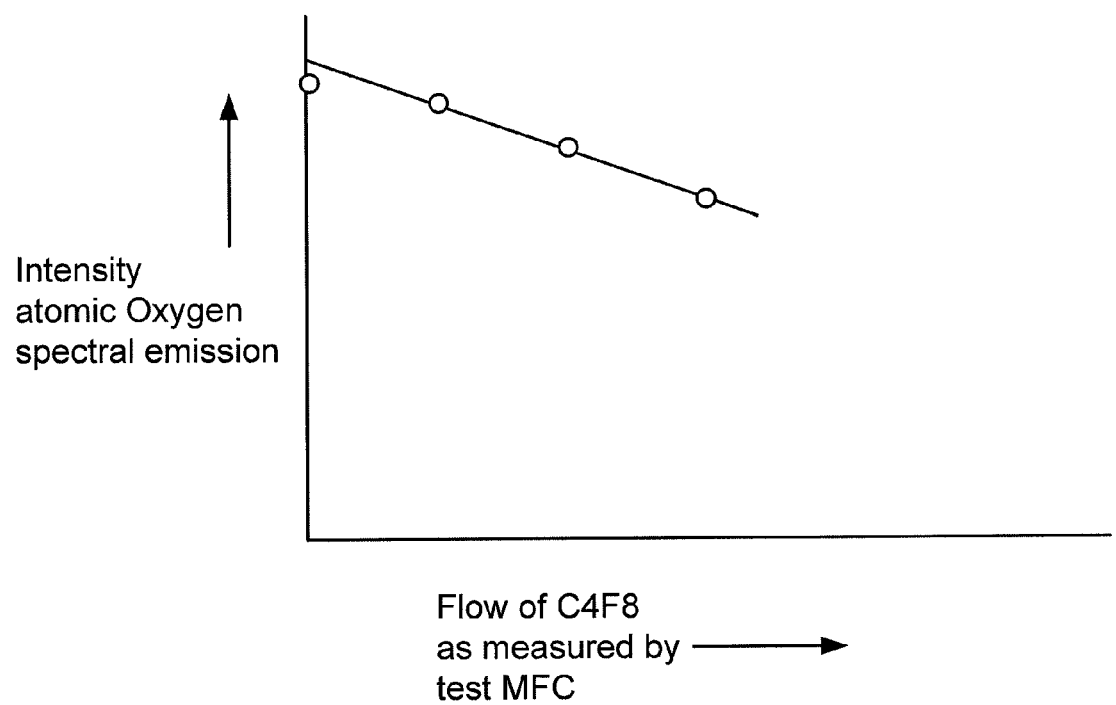
FIG. 4 plots intensity of atomic oxygen spectral emission versus flow of $C_4F_8$ as measured by a test mass flow controller.

The data from this experiment are shown schematically in FIG. 4. From this data, the offset error in the MFC can be deduced by comparing the measurement at no Freon flow, with the extrapolation back to zero of the points at finite gas flow. This zero point determination can also be used to correct the non-linear behavior of the MFC at low flow rates. Further, by comparing the slope of the linear portion of the curve for finite Freon flows, with the slope given by a reference MFC, errors in the MFC caused by an incorrect proportionality calibration constant can be deduced.

In another example, a Freon gas is introduced in successively increasing flow rates into a mixture of argon and oxygen, and an argon line is monitored. In this example, the argon concentration at constant pressure reflects the complement of the concentrations of all the other species present in the neutral gas in the plasma region.

There are several competing effects in this example as the Freon gas flow is increased. There is a dilution effect of the argon concentration in the absence of any chemical reactions as the Freon flow is increased. There is also a decrease in the atomic and molecular oxygen concentration, and an increase in the concentration of reaction by-products such as carbon monoxide, $CF_4$, $COF_2$ and $F_2$.

A first principles model for this situation would be complex and subject to error. In this case, an empirical model would be preferable. Such an empirical model could be constructed by measuring the brightness of, for example, an argon line for varying Freon gas flows using calibrated flow meters.

By comparing the slope of the change in brightness of an argon line versus Freon gas flow against a reference slope generated using reference flow meters for the three gases, a discrepancy between reference and test flow meters can be determined. As in the example above, by comparing the value of the argon line at no Freon flow with the extrapolation to zero from data points at finite Freon flows, we can determine the offset of the calibration curve.

It should also be noted that embodiments in accordance with the present invention are generally applicable to the measurement of different gases made using a variety of types of instruments sensitive to the gas concentration. Alternatives to OES for measuring gas concentration include, but are not limited to mass spectrometry and Fourier transform infrared (FT-IR) spectrometry.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method to determine the flow rate of a second gas relative to a first gas, the method comprising:

setting a flow of a first gas to a known level;

taking a first measurement of the first gas with a measurement technique sensitive to a concentration of the first gas;

establishing a flow of a second gas mixed with the first gas;

taking a second measurement of the first gas with a measurement technique that is sensitive to the concentration of the first gas; and determining the flow of the second gas by a calculation involving a difference between the first measurement and the second measurement, where the first and second gases are used in the manufacture of semiconductor devices.

2. The method of claim 1 where the measurement technique comprises optical emission spectroscopy.

3. The method of claim 1 where the measurement technique is mass spectrometry.

4. The method of claim 1 where the measurement technique is Fourier transform infrared spectroscopy.

5. The method of claim 1 wherein the gases are used in a plasma processing.

6. The method of claim 5 where the gases are used in plasma etching.

7. The method of claim 6 where the first gas comprises a gas mixture.

8. A method comprising:
flowing a first gas into a chamber through a first mass flow controller;
taking a first measurement of the first gas with a measurement technique sensitive to a concentration of the first gas;
flowing a second gas into the chamber through a second mass flow controller;
taking a second measurement of the first gas with the measurement technique; and
determining a flow rate of the second gas relative to the first gas based upon a difference between the first measurement and the second measurement, the method further comprising repeating the above steps with a changed flow rate of the second gas through the second mass flow controller to compile a calibration curve of flow rates of the second mass flow controller.

9. A method comprising:
flowing a first gas into a chamber through a first mass flow controller;
taking a first measurement of the first gas with a measurement technique sensitive to a concentration of the first gas;
flowing a second gas into the chamber through a second mass flow controller;
taking a second measurement of the first gas with the measurement technique; and
determining a flow rate of the second gas relative to the first gas based upon a difference between the first measurement and the second measurement, wherein an absolute magnitude of the rate of flow of the first gas through the mass flow controller is known, the method further comprising determining an absolute magnitude of the flow rate of the second gas through the second mass flow controller.

10. The method of claim 9 wherein the first gas comprises a noble or unreactive gas.

11. The method of claim 9 wherein the flow rate of the second gas relative to the first gas is determined from a first principles model.

12. The method of claim 9 wherein the flow rate of the second gas relative to the first gas is determined from an empirical model.

13. A method comprising:
flowing a first gas into a chamber through a first mass flow controller;
taking a first measurement of the first gas with a measurement technique sensitive to a concentration of the first gas;
flowing a second gas into the chamber through a second mass flow controller;
taking a second measurement of the first gas with the measurement technique; and
determining a flow rate of the second gas relative to the first gas based upon a difference between the first measurement and the second measurement, wherein taking the second measurement comprises:
exposing a sample of a mixture of the first and second gases to a plasma; and
performing optical emission spectroscopy on the exposed sample.

14. The method of claim 13 wherein the first gas is reactive with the second gas.

15. A method comprising:
flowing a first gas into a chamber through a first mass flow controller;
taking a first measurement of the first gas with a measurement technique sensitive to a concentration of the first gas;
flowing a second gas into the chamber through a second mass flow controller;
taking a second measurement of the first gas with the measurement technique; and
determining a flow rate of the second gas relative to the first gas based upon a difference between the first measurement and the second measurement, the method further comprising:
removing the first and second gases from the chamber;
flowing the second gas into the chamber through the second mass flow controller;
taking a third measurement of the second gas with a measurement technique sensitive to a concentration of the second gas;
flowing the first gas into the chamber through the first mass flow controller;
taking a fourth measurement of the second gas with the measurement technique sensitive to the concentration of the second gas; and
determining a flow rate of the first gas relative to the second gas based upon a difference between the third measurement and the fourth measurement; and
reducing an error by comparing the flow rate of the second gas relative to the first gas, with the flow rate of the first gas relative to the second gas.

16. The method of claim 8 wherein the first gas comprises a noble or unreactive gas.

17. The method of claim 8 wherein the flow rate of the second gas relative to the first gas is determined from a first principles model.

18. The method of claim 8 wherein the flow rate of the second gas relative to the first gas is determined from an empirical model.

19. The method of claim 8 wherein taking the second measurement comprises:
exposing a sample of a mixture of the first and second gases to a plasma; and
performing optical emission spectroscopy on the exposed sample.

20. The method of claim 19 wherein the first gas is reactive with the second gas.

21. The method of claim 13 wherein the first gas comprises a noble or unreactive gas.

22. The method of claim 13 wherein the flow rate of the second gas relative to the first gas is determined from a first principles model.

23. The method of claim 13 wherein the flow rate of the second gas relative to the first gas is determined from an empirical model.

24. The method of claim 13 wherein taking the second measurement comprises:
    exposing a sample of a mixture of the first and second gases to a plasma; and
    performing optical emission spectroscopy on the exposed sample.

25. The method of claim 15 wherein the first gas is reactive with the second gas.

26. The method of claim 15 wherein the first gas comprises a noble or unreactive gas.

27. The method of claim 15 wherein the flow rate of the second gas relative to the first gas is determined from a first principles model.

28. The method of claim 15 wherein the flow rate of the second gas relative to the first gas is determined from an empirical model.

29. The method of claim 15 wherein taking the second measurement comprises:
    exposing a sample of a mixture of the first and second gases to a plasma; and
    performing optical emission spectroscopy on the exposed sample.

30. The method of claim 29 wherein the first gas is reactive with the second gas.

* * * * *